(12) United States Patent
Cheng

(10) Patent No.: US 6,509,748 B1
(45) Date of Patent: Jan. 21, 2003

(54) BODY FAT MEASURING DEVICE

(75) Inventor: Ann-Che Cheng, Sanchung (TW)

(73) Assignee: Bion Canada Inc., Toronto (CA)

( * ) Notice: Subject to any disclaimer, the term of this patent is extended or adjusted under 35 U.S.C. 154(b) by 0 days.

(21) Appl. No.: 09/906,737

(22) Filed: Jul. 18, 2001

(51) Int. Cl.⁷ .......................... G01R 27/26; A61B 5/05
(52) U.S. Cl. .................... 324/696; 324/692; 600/547
(58) Field of Search ................................ 600/546, 547, 600/548; 324/696, 692, 693, 694

(56) References Cited

U.S. PATENT DOCUMENTS

| | | | |
|---|---|---|---|
| 5,335,667 A | * 8/1994 | Cha et al. | 600/547 |
| 6,188,925 B1 | 2/2001 | Kawanishi et al. | 600/547 |
| 6,265,882 B1 | * 7/2001 | Madsen et al. | 324/692 |

* cited by examiner

*Primary Examiner*—Christine K. Oda
*Assistant Examiner*—Vincent Q. Nguyen
(74) *Attorney, Agent, or Firm*—Jacobson Holman PLLC

(57) ABSTRACT

A body fat measuring device mainly including a display screen and several control keys disposed on a housing body, one electrode on a frontage of the housing body and two electrodes on a bottom side of the housing body; to use the mentioned structure, user's thumbs press on the electrodes on the frontage of the housing body while the index fingers and the middle fingers press on the bottom side of the housing body to enable a current to transmit into the human body through the electrodes then flow back to the detecting circuit, a voltage drop generated thereby is utilized to calculate an electric resistance value of the human body, then data of a height, a weight, an age and the like are input, a body fat ratio is precisely calculated through a body fat ratio calculating programming and displayed on the display screen.

2 Claims, 6 Drawing Sheets

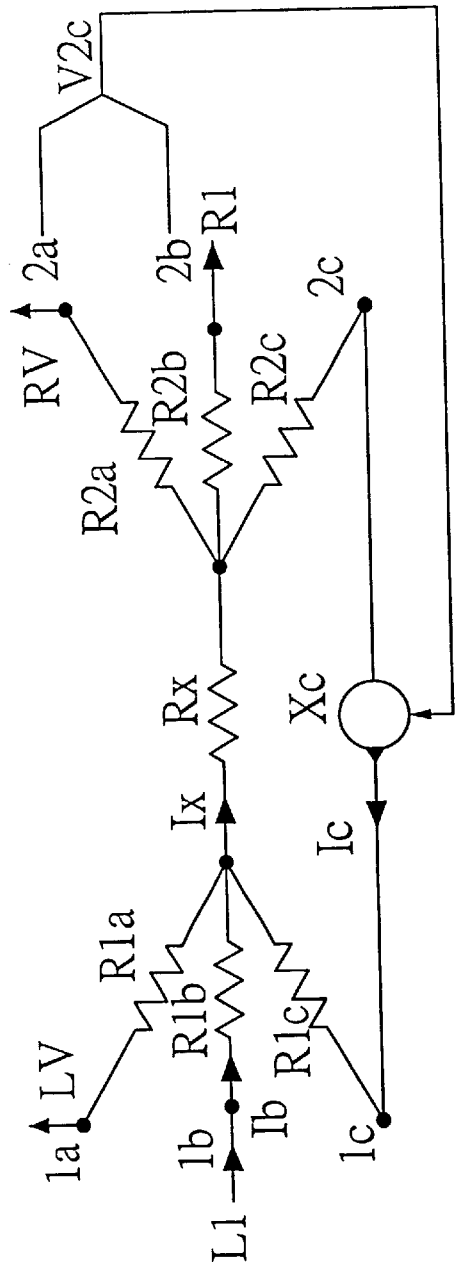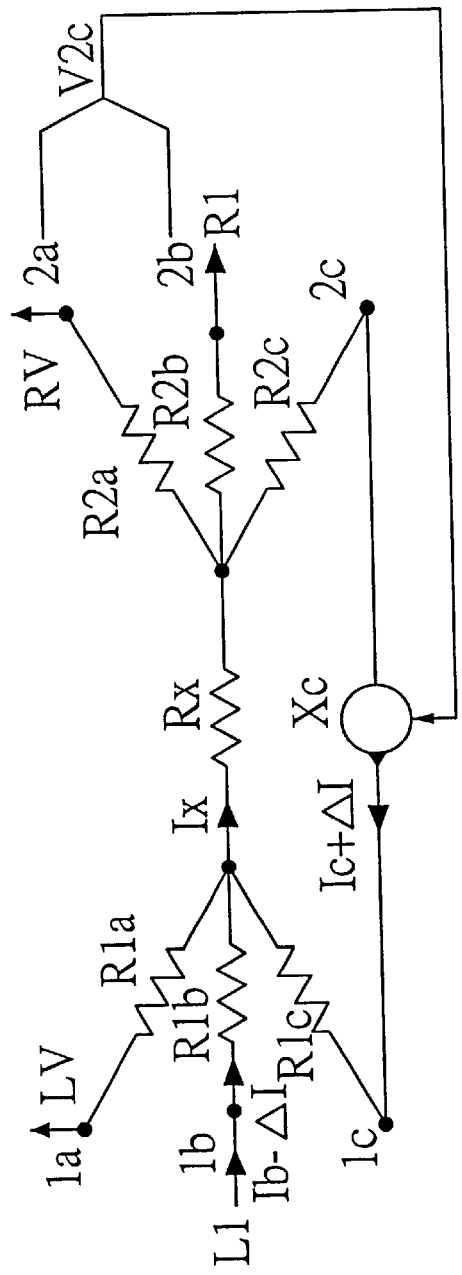
Fig.2(a)
Fig.2(b)

BODY FAT MEASURING DEVICE

BACKGROUND OF THE INVENTION

1) Field of the Invention

The present invention provides a body fat measuring device, more especially a six-point and impedance-input type body fat measuring apparatus with simple structure and convenience for use, capable of rapidly and precisely calculating the content of personal body fat.

2) Description of the Prior Art

Accordingly, modern people pay more attention on their own body figures and health, young women care even more about it, particularly. There is an extremely close relationship between the high or low body fat ratio and the health. Neither too fat nor too skinning is considered ideal. The proper value of the body fat ratio has been determined through many experts' studies. Generally, 70% of the human body content is water. Although water is not a conductor, it contains acid, alkali or salinity which tend to be electrically conductive and have lower electric resistance value; however, fat does not tend to be electrically conductive and has higher electric resistance value; therefore, the magnitude of the human body impedance can be used for calculating the body fat ratio thereof. Furthermore, since the ratio of the impedance to the length is direct and to the sectional area is inverse, people of the same gender, age, height and weight with bigger impedance usually have higher fat ratio; the way of calculating has been determined by many experts' studies.

Presently, there is a published structure with U.S. Pat. No. 6,188,925, wherein the detecting circuit, as shown in FIG. 4, is a four-point type impedance-input means with four electrodes, 1a, 1b, 2a and 2b; contact points (B) of the four electrodes are disposed respectively at the corresponding positions on the upper and the lower sides of a housing body (A), as shown in FIGS. 5 and 6; when in use, due to the improper gesture of the user's hands pressing the electrodes, as shown by the dotted lines in FIGS. 5 and 6, and because the electric conductivity at the tip and on the side of an index finger is much less than that of a normal web section of an index finger, therefore error of measuring value tends to occur and affects the accuracy of the detected result; furthermore, experiments show that in using the four-point type impedance detecting circuit, the augmentation of the contact electric resistance between the fingers and the electrodes also affect the accuracy of the detected result. That does not complies with practicality and needs to be improved.

SUMMARY OF THE INVENTION

The primary objective of the present invention is to provide a body fat measuring device which is a hand-held body fat measuring apparatus, the user has to press his or her thumbs, index fingers and middle fingers simultaneously on the six electrode contact points disposed respectively on the upper and the lower sides of the measuring device for maintaining the advantages of having correct gesture during measuring as well as good and specific contact to lower the percentage value of the end voltage drop of the impedance and so as to have more precise body fat measuring device.

In order to achieve the mentioned objective, the present invention utilizes Bioelectrical Impedance Analysis (BIA) to determine body fat, mainly it has a display screen and several keys disposed on a housing body, three electrodes are disposed respectively on each external section of two sides of the said housing body, the electrode positions on each side are that one on the frontage of the housing body and two on the bottom sides of the housing body, every mentioned component respectively connects and composes with a detecting circuit board inside the housing body.

To use the mentioned structure, after the user activates the power source and makes it enter the movement of measuring through setting and controlling, his or her thumbs, index fingers and middle fingers respectively touch the electrodes on the two sides of the housing body of the said measuring device, the thumbs press on the electrodes on the frontage of the housing body, the index fingers and the middle fingers press on the bottom side of the housing body to enable a current to transmit into the human body through the electrodes then flow back to the detecting circuit, a voltage drop generated thereby is utilized to calculate an electric resistance value of the human body, then data of a height, a weight, an age and the like are input, so that a body fat ratio is precisely calculated through a body fat ratio calculating programming and displayed on the display screen.

BRIEF DESCRIPTION OF THE DRAWINGS

FIG. 2 is a drawing of the circuit of the six-point type impedance detecting circuit of the present invention.

DETAILED DESCRIPTION OF THE PREFERRED EMBODIMENTS

Figure 1:
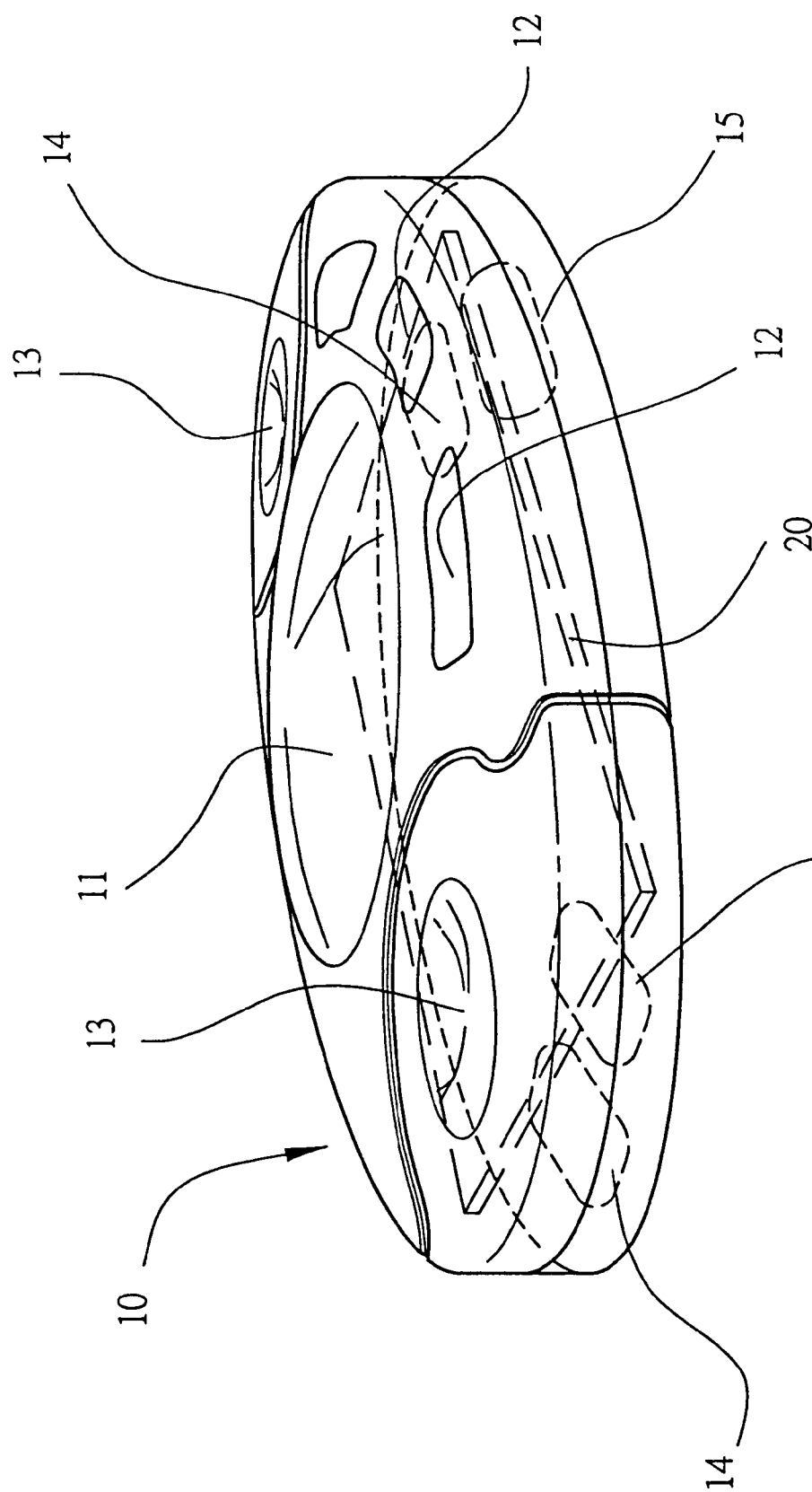
FIG. 1 is a pictorial drawing of the present invention.
Figure 3:
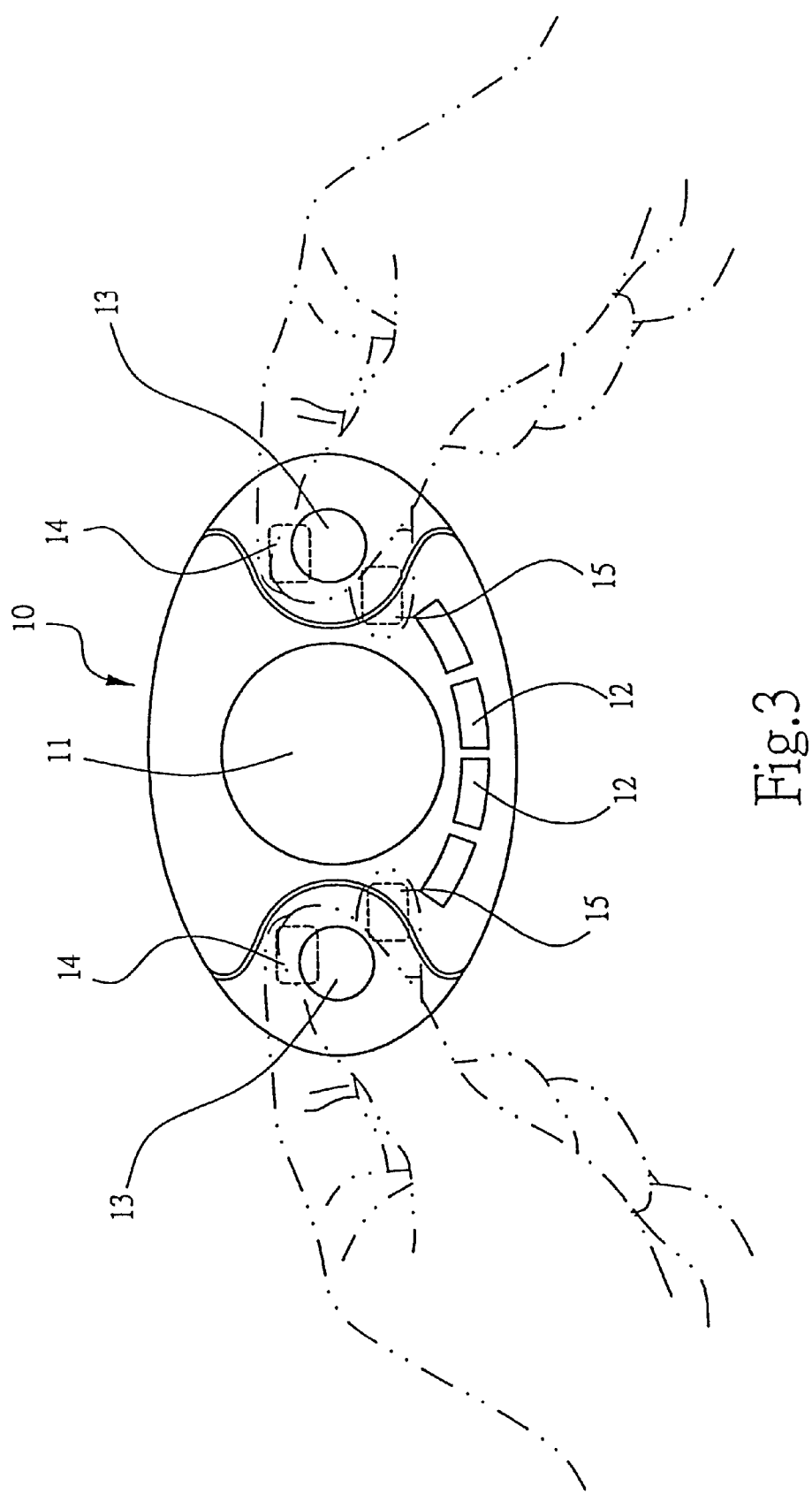
FIG. 3 is a schematic drawing of the plane embodiment of the present invention.
Figure 4A:
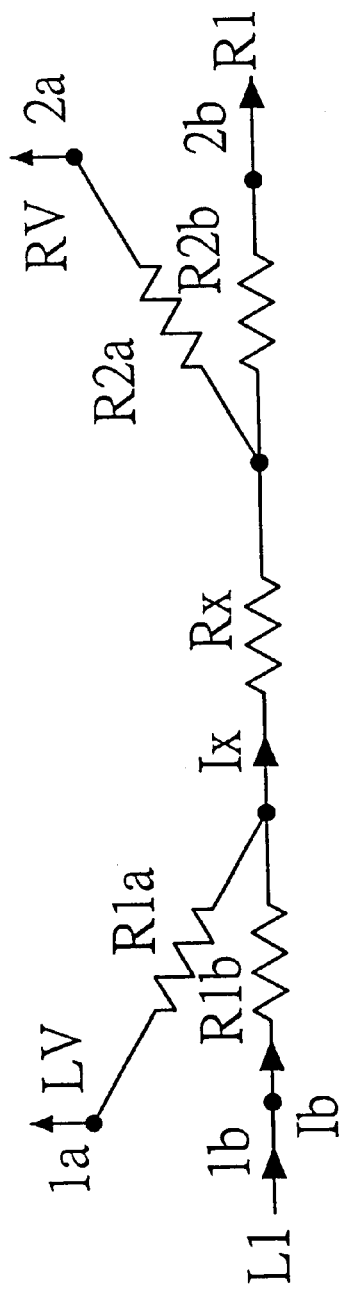
FIG. 4 is a drawing of the circuit of the four-point type impedance detecting circuit of a conventional invention.
Figure 4B:
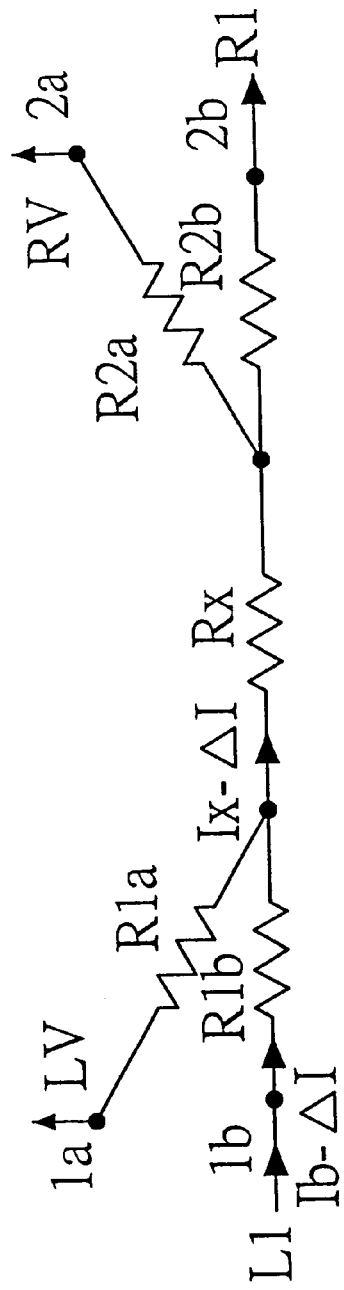

Referring to FIGS. 1 and 3, the present invention of a body fat measuring device mainly comprises of a display screen (11) and several control keys (12) disposed on a housing body (10), as well as three electrodes (13, 14, 15) disposed respectively on each external section of two sides of the said housing body (10); one electrode (13) is disposed on the frontage of each side of the said housing body (10), two electrodes (14, 15) are disposed on the bottom sides thereof; a detecting circuit board (20) mounted inside the said housing body (10) connects and composes with the mentioned parts of the display screen (11), the control keys (12) and the electrodes (13, 14, 15).

To use the mentioned structure, after the user activates the power source and makes it enter the movement of measuring through setting and controlling, his or her thumbs, index fingers and middle fingers press on six electrodes (13, 14, 15) corresponding up-and-down on two sides of the said housing body (10) simultaneously (fingers' holding manner indicated in FIG. 3); after the current transmits into the human body through the electrode (14) on the left-hand side and flows back to the impedance detecting circuit of the detecting circuit board (20) through the electrode (14) on the right-hand side, the voltage drop generated by the electrodes (13) on both the left-hand and the right-hand sides is used to calculate the electric resistance value of the human body to be precisely calculated with the data of a height, a weight, an age and the like pre-input through the control keys (12) to obtain the correct body fat content, and the measured data is displayed on the display screen (11) outside the housing body (10).

Figure 5:
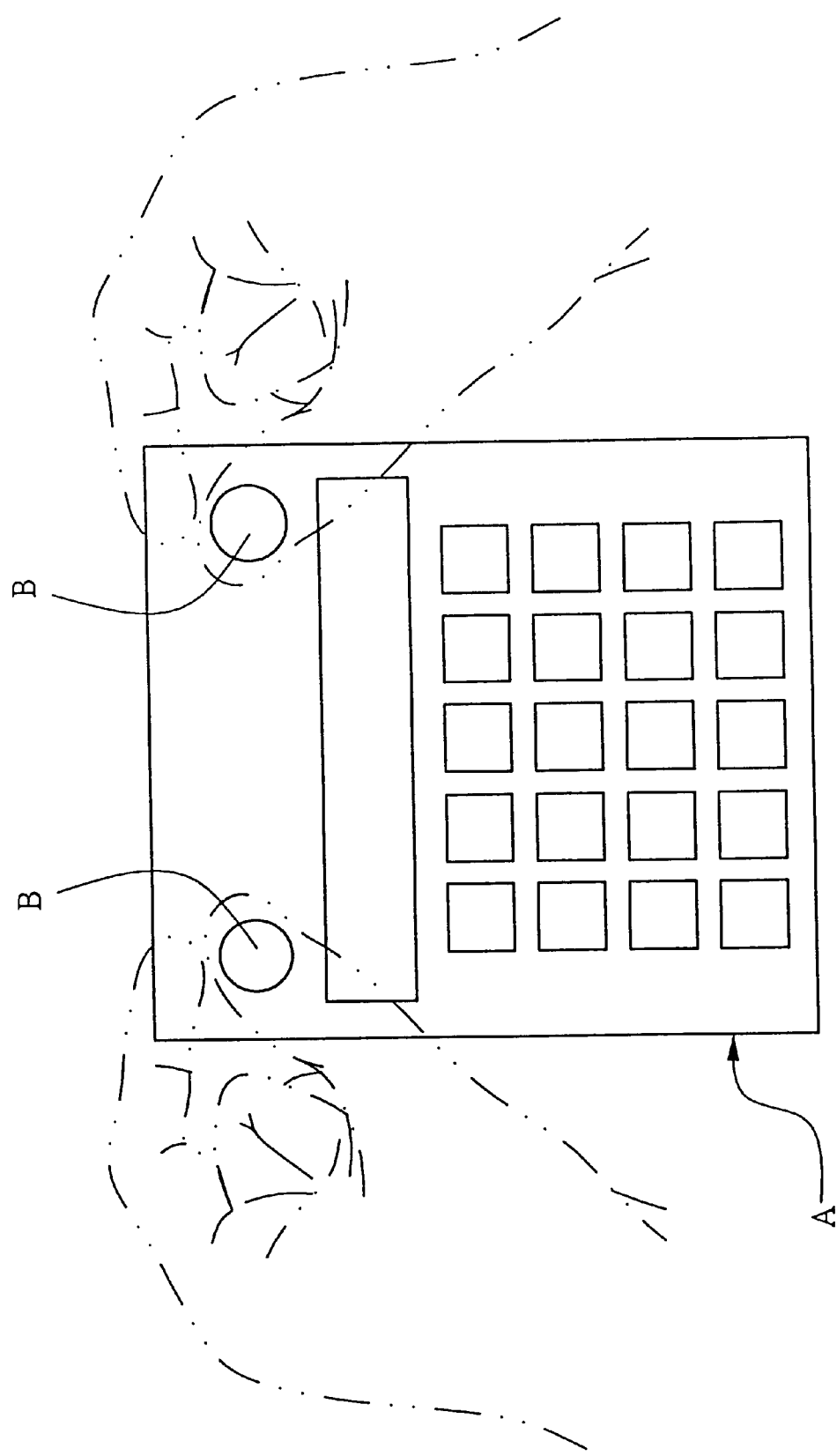
FIG. 5 is a schematic drawing of the application state of a conventional structure.
Figure 6:
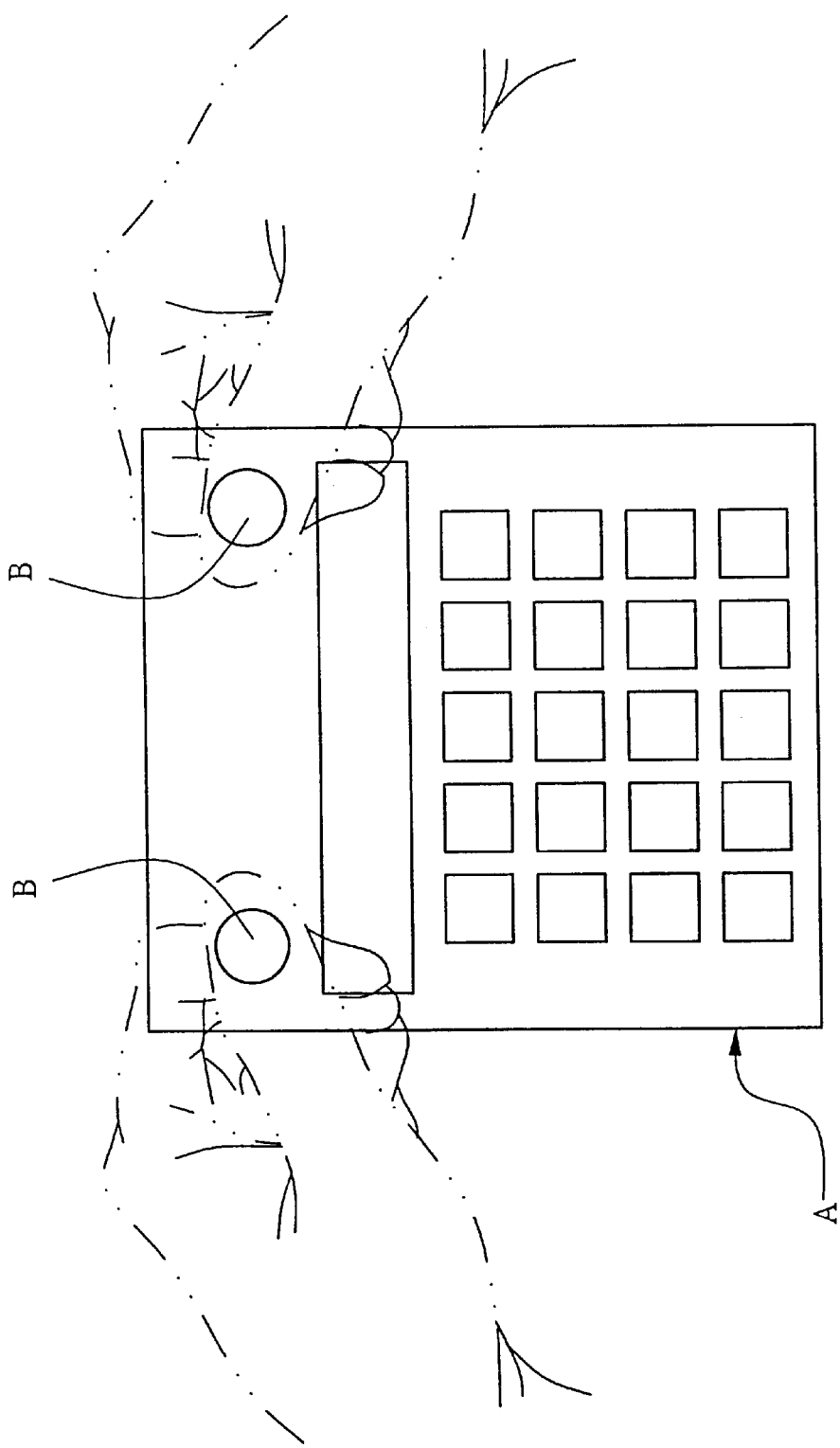
FIG. 6 is a schematic drawing of another application state of a conventional structure.

To compare the present invention as shown in FIG. 3 with the conventional structure as shown in FIGS. 5 and 6, in order to reduce the error, the body fat measuring means using finger contacting method should reduce the contact impedance between the fingers and the electrodes, therefore, the contact area between the fingers and the electrodes should be contacted by the frontage of the web sections of the fingers; however, for the conventional four-point type device, it is very possible to have the shortcoming of causing the sides or the tips of the fingers to come in contact; the six-point type structure of the present invention possessing the advantages of guiding the user to use the correct gesture and contact areas to press the electrodes because it has proper arrangement for the electrode positions.

Referring to FIG. 2, the drawing of the circuit of the six-point type impedance detecting circuit of the present invention, wherein $1a$, $1b$, $1c$, $2a$, $2b$, and $2c$ denotes the six contact points of the electrodes, the advantages thereof are that error caused by contact impedance between the fingers and the electrodes can be prevented and when the contact electric resistance increases too much to maintain a state of constant current, the current compensating circuit specifically set between electrodes $1c$ and $2c$ can prevent the measured bioelectrical impedance from causing error; when the contact electric resistance increases to make the current of the constant current power source slightly decrease, the current of the current compensating circuit also slightly increases due to the augmentation of the contact electric resistance so as to keep the current past by the body impedance stay almost unchanged; proper adjustment can suitably compensate the mentioned error to be above the maximum range of the general human body contact electric resistance.

As mentioned, alternating current is used to measure the bioelectrical impedance because using the direct current, most of the externally added voltage might be offset by the counter electromotive force due to the effect of counter electromotive force of electrolysis, polarization and the like, so the electric resistance value obtained from dividing the voltage by the current will be far bigger than the actual electric resistance value (impedance value) and that will affect the detected accuracy. Therefore, based on studies, using 50 kHz alternating current power source as the testing power source can obtain the best sensibility and accuracy. In order to reduce the error caused by the contact electric resistance, the present invention has a six-point type impedance input means with several electrodes (13, 14, 15) disposed respectively on the upper and the lower sides of the two sides of the housing body (10) and uses the digital impedance detecting circuit to reduce the influence of the contact electric resistance to the least.

Therefore, the present invention alternates the alternating current power source (50 kHz alternating current sine wave) used for measuring the human body impedance to a constant current power source to be added between the electrodes $1b$ and $2b$, referring to FIG. 2, the voltage Vx generated by this current passing through the human body impedance Rx is further guided and connected at the electrodes $1a$ and $2a$ to the voltage measuring circuit formed by OP AMP; under an ideal condition, the current caught by the voltage circuit is very little and ignorable, at this time, the measured voltage is the voltage Vx at the two ends of Rx, this voltage does not include contact electric resistance R$1b$ and R$2b$; under the constant current, the ratio of Vx to Rx is direct and can be further compared with the standard electric resistance of the known electric resistance value to obtain the Rx value.

Only under a not absolute ideal condition, no matter how high the sensibility of OP AMP is, it is still necessary to use some current; on the aspect of the contact electric resistance, under the situation when the skin surface of the human body is very dry, it is possible that the constant current circuit becomes incapable of maintaining constant current due to too big contact electric resistance. When exceeding the limit of the constant current, the bigger the contact electric resistance, the smaller the measured body electric resistance (Rx) will be; the present invention utilizes the current compensating circuit formed by $1c$, $2c$ and Xc to compensate this error, when the contact electric resistance R$1b$ and R$2b$ increase, the end voltage V$2c$ also increase in ratio to make the compensating current Ic increase; proper adjustment can make the current passing through the body impedance maintain almost unchanged so as to eliminate the error occurrence.

As mentioned, when the constant current exceeds the maximum limit of the constant current, the current reduces gradually, at this time, the voltage for measuring the bio-electrical impedance (Rx) reduces or increases along with the magnitude of the contact electric resistance (R$1a$ and R$1b$) thereby affects the accuracy of Rx, the situation of using the four-point type and six-point type electrodes is described comparatively as follows:

The situation of using four-point-types electrodes is that when contact electric resistance increases to make the current reduce from Ib to Ib−ΔI, as shown in FIGS. $4a$ and $4b$, the current past by the body impedance also reduces from Ix to Ix∆×I, which represents that the end voltage of the human body reduces also in ratio to make the measured body impedance reduce and thereby affect the accuracy.

The situation of using six-point type electrodes is that when the contact electric resistance increases to make the current reduce from Ib to Ib−ΔI, as shown in FIGS. $2a$ and $2b$, the increase of the end voltage V$2c$ of $2a$ and $2b$ makes the compensating current Ic increase to Ic+ΔI, however, the current Ix past by the body impedance stay almost the same, therefore the drop rate of the end voltage thereof is smaller and the accuracy is preferred.

In summation of the foregoing sections, the present invention is capable of specifically achieving the objective of precisely calculating the personal body fat ratio; therefore, the present invention complies with the important elements of practicality and advancement regulated by the patent law; since the structure and the configuration of the present invention has not been publicly used or disclosed in printed material prior to the submission for new patent application, the invention is innovative. However, the forgoing description is merely one of the preferred exemplary embodiments of the present invention, to those skilled in the art, any modification or changes with equal effect based on the spirit of the present invention should all be included in the following scope of the claim application of the present invention.

What is claimed is:

1. A body fat measuring device comprising of a detecting circuit board disposed inside a housing body is characterized that:

three electrodes are disposed respectively on each external section on two sides of the said housing body; the positions of the electrodes on each side form a six-point structure impedance input means with one electrode on the frontage of the housing body and two electrodes on the bottom side of the housing body; each said electrode connects respectively with the detecting circuit board mounted inside the housing body.

2. A body fat measuring device according to claim 1, wherein after the user activates the power source user's thumbs, index fingers and middle fingers respectively touch the electrodes on the two sides of the housing body of the said measuring device, the thumbs press on the electrodes on the frontage of the housing body, the index fingers and the middle fingers press on the bottom side of the housing body to enable a current to transmit into the human body through the electrodes then flow back to the detecting circuit, a voltage drop generated thereby is utilized to calculate an electric resistance value of the human body, then data of a height, a weight, an age are input, thereby a body fat ratio is precisely calculated through a body fat ratio calculating programming and displayed on a display screen.

* * * * *